US006642411B1

(12) United States Patent
Leone-Bay et al.

(10) Patent No.: US 6,642,411 B1
(45) Date of Patent: Nov. 4, 2003

(54) COMPOUNDS AND COMPOSITIONS FOR DELIVERING ACTIVE AGENTS

(75) Inventors: Andrea Leone-Bay, Ridgefield, CT (US); Doris O'Toole, Carmel, NY (US)

(73) Assignee: Emisphere Technologies, Inc., Tarrytown, NY (US)

( * ) Notice: Subject to any disclaimer, the term of this patent is extended or adjusted under 35 U.S.C. 154(b) by 0 days.

(21) Appl. No.: 09/744,862

(22) PCT Filed: Jul. 27, 1999

(86) PCT No.: PCT/US99/17090
§ 371 (c)(1),
(2), (4) Date: Apr. 19, 2001

(87) PCT Pub. No.: WO00/06534
PCT Pub. Date: Feb. 10, 2000

Related U.S. Application Data
(60) Provisional application No. 60/104,466, filed on Oct. 16, 1998, and provisional application No. 60/094,267, filed on Jul. 27, 1998.

(51) Int. Cl.[7] .................. C07C 229/00; A01N 37/12
(52) U.S. Cl. .................. 562/455; 562/451; 514/503
(58) Field of Search ................ 562/455, 457; 514/563

(56) References Cited

U.S. PATENT DOCUMENTS

| | | | |
|---|---|---|---|
| 4,147,767 A | 4/1979 | Yapel | 424/22 |
| 4,238,506 A | 12/1980 | Stach et al. | 424/319 |
| 4,692,433 A | 9/1987 | Hostetler et al. | 514/12 |
| 4,757,066 A | 7/1988 | Shiokari et al. | 514/210 |
| 4,873,087 A | 10/1989 | Morishita et al. | 424/433 |
| 4,895,725 A | 1/1990 | Kantor et al. | 424/455 |
| 4,925,673 A | 5/1990 | Steiner | |
| 4,976,968 A | 12/1990 | Steiner | 424/491 |
| 4,983,402 A | 1/1991 | Steiner | 424/491 |
| 5,066,487 A | 11/1991 | Morelle et al. | 424/68 |
| 5,352,461 A | 10/1994 | Feldstein et al. | 424/493 |
| 5,401,516 A | 3/1995 | Milstein et al. | 424/491 |
| 5,443,841 A | 8/1995 | Milstein et al. | 424/451 |
| 5,447,728 A | 9/1995 | Milstein et al. | 424/490 |
| 5,451,410 A | 9/1995 | Milstein et al. | 424/490 |
| 5,455,335 A | 10/1995 | Kahane et al. | 536/5 |
| 5,540,939 A | 7/1996 | Milstein et al. | 424/491 |
| 5,541,155 A | 7/1996 | Leone-Bay et al. | 514/2 |
| 5,578,323 A | 11/1996 | Milstein et al. | 424/499 |
| 5,601,846 A | 2/1997 | Milstein et al. | 424/499 |
| 5,629,020 A | 5/1997 | Leone-Bay et al. | 424/489 |
| 5,643,957 A | 7/1997 | Leone-Bay et al. | 514/563 |
| 5,650,386 A | 7/1997 | Leone-Bay et al. | 514/2 |
| 5,667,806 A | 9/1997 | Kantor et al. | 424/484 |
| 5,693,338 A | 12/1997 | Milstein et al. | 424/451 |
| 5,705,529 A | 1/1998 | Matyus et al. | 514/541 |
| 5,709,861 A | 1/1998 | Santiago et al. | 424/184 |
| 5,714,167 A | 2/1998 | Milstein et al. | 424/490 |
| 5,750,147 A | 5/1998 | Kantor et al. | 424/491 |
| 5,766,633 A | 6/1998 | Milstein et al. | 424/489 |
| 5,773,647 A | 6/1998 | Leone-Bay et al. | 562/444 |
| RE35,862 E | 7/1998 | Steiner et al. | 424/455 |
| 5,776,888 A | 7/1998 | Leone-Bay et al. | 514/2 |
| 5,792,451 A | 8/1998 | Sarubbi et al. | 424/85.4 |
| 5,804,688 A | 9/1998 | Leone-Bay et al. | 562/444 |
| 5,811,127 A | 9/1998 | Milstein et al. | 424/490 |
| 5,820,881 A | 10/1998 | Milstein et al. | 424/489 |
| 5,824,345 A | 10/1998 | Milstein et al. | 424/489 |
| 5,840,340 A | 11/1998 | Milstein et al. | 424/499 |
| 5,863,944 A | 1/1999 | Leone-Bay et al. | 514/559 |
| 5,866,536 A | 2/1999 | Leone-Bay et al. | 514/2 |
| 5,876,710 A | 3/1999 | Leone-Bay et al. | 424/85.1 |
| 5,879,681 A | 3/1999 | Leone-Bay et al. | 424/85.1 |
| 5,935,601 A | 8/1999 | Leone-Bay et al. | 424/489 |
| 5,939,381 A | 8/1999 | Leone-Bay et al. | 514/2 |
| 5,955,503 A | 9/1999 | Leone-Bay et al. | 514/563 |
| 5,958,457 A | 9/1999 | Santiago et al. | 424/490 |
| 5,962,710 A | 10/1999 | Gschneidner et al. | 554/112 |
| 5,965,121 A | 10/1999 | Leone-Bay et al. | 424/85.2 |
| 5,972,387 A | 10/1999 | Milstein et al. | 424/491 |
| 5,976,569 A | 11/1999 | Milstein et al. | 424/451 |
| 5,989,539 A | 11/1999 | Leone-Bay et al. | 424/85.2 |
| 5,990,166 A | 11/1999 | Leone-Bay et al. | 514/563 |
| 6,001,347 A | 12/1999 | Leone-Bay et al. | 424/85.1 |
| 6,051,258 A | 4/2000 | Kantor | 424/491 |
| 6,051,561 A | 4/2000 | Leone-Bay et al. | 514/56 |
| 6,060,513 A | 5/2000 | Leone-Bay et al. | 514/559 |
| 6,071,510 A | 6/2000 | Leone-Bay et al. | 424/85.2 |
| 6,071,538 A | 6/2000 | Milstein et al. | 424/464 |
| 6,084,112 A | 7/2000 | Ho et al. | 554/114 |
| 6,090,958 A | 7/2000 | Leone-Bay et al. | 554/112 |
| 6,099,856 A | 8/2000 | Milstein et al. | 424/450 |
| 6,100,285 A | 8/2000 | Kantor | 514/400 |
| 6,100,298 A | 8/2000 | Leone-Bay et al. | 514/563 |
| 6,180,140 B1 | 1/2001 | Leone-Bay et al. | 424/489 |
| 6,221,367 B1 | 4/2001 | Milstein et al. | 424/400 |

FOREIGN PATENT DOCUMENTS

| | | | |
|---|---|---|---|
| EP | 0036145 | 9/1981 | |
| EP | 226223 | 6/1987 | |
| EP | 0517211 | 9/1992 | |
| EP | 576941 | 6/1993 | |
| ES | 369853 | 7/1969 | |
| FR | 4446 | 11/1966 | |
| GB | 2095994 | 10/1982 | |
| JP | 48-37819 | 11/1973 | |
| JP | 2239980 | 9/1990 | |
| WO | WO 95/11690 | 5/1995 | A61K/37/00 |

(List continued on next page.)

OTHER PUBLICATIONS

Leone–Bay, A, "4–[40[(2–Hydroxybenzoyl) Amino]phenyl] butyric Acid As A Novel Oral Delivery for Recombinant Human Growth Hormone", J. Medicinal Chemistry, 39:13:2571–2578 (1996).

(List continued on next page.)

*Primary Examiner*—Paul J. Killos
(74) *Attorney, Agent, or Firm*—Darby & Darby (57) ABSTRACT

Carrier compounds and compositions therewith which are useful in the delivery of active agents are provided Methods of administration and preparation are provided as well.

27 Claims, 2 Drawing Sheets

FOREIGN PATENT DOCUMENTS

| WO | WO 96/12473 | 5/1996 | ............ A61K/9/16 |
|----|-------------|--------|-----------------------|
| WO | WO 96/30036 A | 10/1996 | |
| WO | WO 97/36480 A | 10/1997 | |
| WO | WO 99/29705 | 6/1999 | ........... C07H/15/00 |
| WO | 0006184 | 2/2000 | |
| WO | 0006534 | 2/2000 | |
| WO | 0007979 | 5/2000 | |
| WO | 0048589 | 8/2000 | |
| WO | 0059863 | 10/2000 | |

OTHER PUBLICATIONS

Picciola, G, "Sintesi Di Acidi Chinazolinonici E Benzossazinonici E Studio Delle Loro Proprieta Antiinflammatorie", 31:9:655–664 (1976).

Palagiano, F. et al.: "Synthesis, stability and anticonvulsant activity of two new GABA prodrugs," *PHARAMAZIC*, 52 (4): 272–276 (1997), XP–001084051.

Yalcin, I. et al.: "Synthesis and Microbiological Activity of Some Novel N–(2–Hydroxyl–5–Substitutedphenyl)Benzacetamides, Phenoxyacetamides and Thiophenoxycetamides as the Possible Metabolites of Antimicrobial Active Benzoxazoles," *IL FARMACO*, 52 (11), 685–689 (1997).

Chem Abs 73548–12–6 (Apr. 1991).

Chem Abs 70204–54–5 (Apr. 1991).

Chem Abs 184360 –83–342 (1975) Solubility and disassociation constants of some alicyclic acids.

Chemical Abstract, vol. 99(23) Abst. No. 191473h (1983).

Johansen, Marianne, et al. "The Kinetics of decompn. Of various N–Mannich bases of salicylamide" Int. J. Pharm. (1980), 7(2): 119–27 (1980).

Riveria, Theresa M. et al. "Oral Delivery of Heparin in Combination with Sodium N–[8–2–hydroxybenzoyl)amino] caprylate: Pharmacological Considerations" Pharmaceutical Research vol 14(12) 1830–1834 (1997).

Andrea Leone–Bay "4–(4–Salicyloylaminophenyl)butyric Acid as a Novel Oral Delivery Agent for Recombinant Human Growth Hormone" Medi 006, Presented at the American Chemical Society, Mar. 24–28, 1997 New Orleans, LA.

Leone–Bay, A. et al. " The evolution of an oral heparin dosing solution" Drugs of the Future vol 22(8) 885–891 (1997).

Brayden, D. et al. "Heparin Absorption across the intestin: Effects of Sodium N–[8–2hydorxybenzoyl)Amino] Caprylate in rat in situ intestinal instillations ind in Caco–2 monolayers" Pharmaceutical Research vol 14(12) 1772–1779 (1997).

Leone–Bay, A. "Acylated non–alpha–amino acids as novle agents for the oral delivery of heparin sodium, USP" Journal of Controlled Release 50: 41–49 (1998).

Leone–Bay, A. "4–[4–[(2–Hydroxybenzoyl)amino]phenyl] butyric acid as a novel oral delivery agent for recombinant human growth hormone" ; Journal of Medicinal Chemistry vol 39, 2571–2578 (1996).

Leone–Bay, A. "N–Acylated alpha–amino acids as novel oral delivery agents for proteins"; Journal of Medicinal Chemistry vol 38, 4263–4269 (1995).

Leone–Bay, A. "N–Acylated alpha–amino acids as novel oral delivery agents for proteins" ; Journal of Medicinal Chemistry vol 38, 4257–4262 (1995).

Ho Koc–Kan; et al. " A Practical Synthesis of ω–aminoalkanoic acid derivatives form Cycloalkanones" Synthetic Communication, vol. 26, No. 14: 2641–2649 (1996).

Brown, G. and Foubister, A.J. Receptor Binding Sites of Hypoglycemic Sulfonylureas and Related[(Acylamino)alkyl]benzoic Acids JmedChem 27, 79–81 1984.

COMPOUNDS AND COMPOSITIONS FOR DELIVERING ACTIVE AGENTS

This application is a national phase application under 35 U.S.C. §371 of International Application No. PCT/US99/17090, filed Jul. 27, 1999, which was published in English on Feb. 10, 2000 as International Publication No. WO 00/06534 and claims the benefit of U.S. Provisional Application No. 60/094,267, filed Jul. 27, 1998, and U.S. Provisional Application No. 60/104,466, filed Oct. 16, 1998.

FIELD OF THE INVENTION

The present invention relates to compounds for delivering active agents, and particularly biologically or chemically active agents. These compounds are used as carriers to facilitate the delivery of an active agent to a target. The carrier compounds are well suited to form non-covalent mixtures with biologically-active agents for pulmonary, oral, subcutaneous, intranasal, sublingual, buccal, ocular, intracolonic, intraduodenal, rectal, vaginal, mucosal, transdermal, intradermal, parenteral, intravenous, and intramuscular administration to animals, as well as crossing the blood-brain barrier. Methods for the preparation and administration of such compositions are also disclosed.

BACKGROUND OF THE INVENTION

Conventional means for delivering active agents are often severely limited by biological, chemical, and physical barriers. Typically, these barriers are imposed by the environment through which delivery occurs, the environment of the target for delivery, or the target itself. Biologically or chemically active agents are particularly vulnerable to such barriers.

For example, in the delivery to animals of biologically active or chemically active pharmacological and therapeutic agents, barriers are imposed by the body. Examples of physical barriers are the skin and various organ membranes that must be traversed before reaching a target. Chemical barriers include, but are not limited to, pH variations, lipid bi-layers, and degrading enzymes.

These barriers are of particular significance in the design of drug delivery systems. For example, oral delivery of many biologically or chemically active agents would be alternate routes of choice for administration to animals if not for biological, chemical, and physical barriers such as varying pH in the gastro-intestinal membranes. Among the numerous agents which are not typically amenable to oral administration are biologically or chemically active peptides, such as calcitonin and insulin; polysaccharides, and in particular mucopolysaccharides including, but not limited to, heparin; heparinoids; antibiotics; and other organic substances. These agents are rapidly rendered ineffective or are destroyed in the gastro-intestinal tract by acid hydrolysis, enzymes, and the like. In addition, the size and structure of macromolecular drugs may prohibit absorption.

Crossing the blood-brain barrier, as well as oral, subcutaneous, intranasal, sublingual, buccal, ocular, intracolonic, intraduodenal, mucosal, transdermnal or pulmonary delivery to the circulatory system for many biologically active agents could be the route of choice for administration to animals if not for physical barriers such as the skin, lipid bi-layers, and various organ membranes that are relatively impermeable to certain biologically active agents, but one or more of which must be traversed before an agent delivered via these routes can reach the circulatory system. Additionally, delivery such as, for example, sublingual delivery may be impeded by chemical barriers such as the varying pH in the gastrointestinal (GI) tract and the presence of powerful digestive enzymes.

Earlier methods for orally administering vulnerable pharmacological agents have relied on the co-administration of adjuvants (e.g., resorcinols and non-ionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation.

Liposomes have also been described as drug delivery systems for insulin and heparin. See, for example, U.S. Pat. No. 4,239,754; Patel et al. (1976), *FEBS Letters*, Vol. 62, pg. 60; and Hashimoto et al. (1979), *Endocrinology Japan*, Vol. 26, pg. 337.

However, broad spectrum use of such drug delivery systems is precluded because: (1) the systems require toxic amounts of adjuvants or inhibitors; (2) suitable low molecular weight cargos, i.e. active agents, are not available; (3) the systems exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

More recently, microspheres of artificial polymers of mixed amino acids (proteinoids) have been used to deliver pharmaceuticals. For example, U.S. Pat. No. 4,925,673 describes drug-containing proteinoid microsphere carriers as well as methods for their preparation and use. These proteinoid microspheres are useful for the delivery of a number of active agents.

However, there is still a need for simple, inexpensive delivery systems which are easily prepared and which can deliver a broad range of active agents by various routes.

SUMMARY OF THE INVENTION

The present invention provides compounds having the formula and salts thereof. These compounds are useful in the delivery of active agents.

Another embodiment of the invention is a composition comprising:

(A) at least one active agent; and (B) a carrier comprising a compound having the formula or a salt thereof.

Also provided are dosage unit forms comprising the composition above and an excipient, a diluent, a disintegrant, a lubricant, a plasticizer, a colorant, a dosing vehicle, or any combination thereof.

Methods for administering a biologically-active agent to an animal in need of the agent by the pulmonary, oral, subcutaneous, intranasal, sublingual, buccal, ocular, intracolonic, intraduodenal, rectal, vaginal, mucosal, transdermal, intradermal, parenteral, intravenous, or intramuscular route or crossing the blood-brain barrier with the compositions of the present invention are also provided.

DETAILED DESCRIPTION OF THE INVENTION

One group of compositions of the present invention include an active agent and a carrier which includes the compound 2-(4-(N-salicyloyl)aminophenyl)propionic acid or salts thereof, such as the sodium salt thereof (sodium 2-(4-(N-salicyloyl)aminophenyl)propionate). These compositions may be used to deliver various active agents through various biological, chemical, and physical barriers and are particularly suited for delivering active agents which are subject to environmental degradation. The compositions of the subject invention are particularly useful for delivering or administering biologically or chemically active agents to any animals such as birds, including, but not limited to, chickens; mammals, such as primates, and particularly humans; and insects.

Other advantages of the present invention include the use of easy to prepare, inexpensive raw materials. The compositions and the formulation methods of the present invention are cost effective, simple to perform, and amenable to industrial scale up for commercial production.

Pulmonary, oral, subcutaneous, intranasal, sublingual, buccal, ocular, intracolonic, intraduodenal, rectal, vaginal, mucosal, transdermal, intradermal, parenteral, intravenous, and intramuscular coadministration of an active agent, such as, for example, recombinant human growth hormone (rhGH); salmon calcitonin; insulin heparin, including, but not limited to, low molecular weight heparin and very low molecular weight heparin; parathyroid hormone (PTH); and compounds in compositions as described herein result in an increased bioavailability of the active agent compared to administration of the active agent alone.

Active Agents

Active agents suitable for use in the present invention include biologically and chemically active agents including, but not limited to, cosmetics, pesticides, pharmacological agents, and therapeutic agents. For example, biologically or chemically active agents suitable for use in the present invention include, but are not limited to, proteins; polypeptides; peptides, and particularly small peptides; hormones, and particularly hormones which by themselves do not or only a fraction of the administered dose passes through the gastro-intestinal mucosa and/or are susceptible to chemical cleavage by acids and enzymes in the gastro-intestinal tract; polysaccharides, and particularly mixtures of much-polysaccharides; carbohydrates; lipids; other organic compounds; or any combination thereof. Further examples include, but are not limited to, the following, including synthetic, natural or recombinant sources thereof: growth hormones, including human growth hormones (hGH), recombinant human growth hormones (rhGH), bovine growth hormones, and porcine growth hormones; growth hormone-releasing hormones; interferons, including α, β and γ; interleukin-1; interleukin-II; insulin;insulin-like growth factor, including IGF-1; heparin, including unfractionated heparin, heparinoids, dermatans, chondroitins, low molecular weight heparin, very low molecular weight heparin and ultra low molecular weight heparin; calcitonin, including salmon, eel and human; erythropoietin (EPO); atrial naturetic factor; antigens; monoclonal antibodies; somatostatin; protease inhibitors; adrenocorticotropin, gonadotropin releasing hormone; oxytocin; leutinizing-hormone-releasing-hormone; follicle stimulating hormone; glucocerebrosidase; thrombopoietin; filgrastim; prostaglandins; cyclosporin; vasopressin; cromolyn sodium (sodium or disodium chromoglycate); vancomycin; desferrioxamine (DFO); parathyroid hormone (PTH), including its fragments; antimicrobials, including anti-fungal agents; analogs, fragments, mimetics or polyethylene glycol (PEG)-modified derivatives of these compounds; or any combination thereof.

Carriers

The carrier compounds of the present invention include 2-(4-(N-salicyloyl)aminophenyl)propionic acid and salts thereof. Salts of the compound include, but are not limited to, organic or inorganic salts, such as the sodium salt:

Sodium-2-(4-(N-salicyloyl)aminophenyl)propionate

In addition, carriers of the present invention include poly amino acids and peptides comprising one or more of the carrier compounds of the present invention.

These carrier compounds, poly amino acids, and peptides may be used to deliver active agents including, but not limited to, biologically or chemically active agents, such as for example, pharmacological and therapeutic agents.

An amino acid is any carboxylic acid having at least one free amine group and includes naturally occurring and synthetic amino acids.

Poly amino acids are either peptides or two or more amino acids linked by a bond formed by other groups which can be linked, e.g., an ester, anhydride, or an anhydride linkage.

Peptides are two or more amino acids joined by a peptide bond. Peptides can vary in length from dipeptides with two amino acids to polypeptides with several hundred amino acids. See *Chambers Biological Dictionary*, editor Peter M. B. Walker, Cambridge, England: Chambers Cambridge, 1989, page 215. Special mention is made of di-peptides, tri-peptides, tetra-peptides, and penta-peptides.

The carriers described herein may be derived from amino acids and can be readily prepared from amino acids by methods within the skill of those in the art based upon the present disclosure and the methods described in WO96/30036, WO97/36480, U.S. Pat. Nos. 5,643,957 and 5,650,386. For example, the compounds may be prepared by reacting the single amino acid, mixtures of two or more amino acids, or amino acid esters with the appropriate acylating or amine-modifying agent, which reacts with a free amino moiety present in the amino acid to form amides. Protecting groups may be used to avoid unwanted side reactions as would be known to those skilled in the art. With regard to protecting groups, reference is made to T. W. Greene, *Protecting Groups in Organic Synthesis*, Wiley, New York (1981), the disclosure of which is hereby incorporated herein by reference.

Suitable, but not limiting, examples of acylating agents useful in preparing an acylated amino acids include the acid chloride acylating agents having the formula wherein $R^1$ is an appropriate group for the modified amino acid being prepared, such as, but not limited to, alkyl, alkenyl, cycloalkyl, or aromatic, and particularly methyl, ethyl, cyclohexyl, cyclophenyl, phenyl, or benzyl, and X is a leaving group. Typical leaving groups include, but are not limited to, halogens such as chlorine, bromine and iodine.

Examples of the acylating agents include, but are not limited to, acyl halides including, but not limited to, acetyl chloride, propyl chloride, cyclohexanoyl chloride, cyclopentanoyl chloride, and cycloheptanoyl chloride, benzoyl chloride, hippuryl chloride and the like; and anhydrides, such as acetic anhydride, propyl anhydride, cyclohexanoic anhydride, benzoic anhydride, hippuric anhydride and the like. Preferred acylating agents include benzoyl chloride, hippuryl chloride, acetyl chloride, cyclohexanoyl chloride, cyclopentanoyl chloride, and cycloheptanoyl chloride.

The amine groups can also be modified by the reaction of a carboxylic acid with coupling agents such as the carbodiimide derivatives of amino acids, particularly hydrophilic amino acids such as phenylalanine, tryptophan, and tyrosine. Further examples include dicyclohexylcarbodiimide and the like.

If the amino acid is multifunctional, i.e., has more than one —OH, —NH, or —SH group, then it may optionally be acylated at one or more functional groups to form, for example, an ester, amide, or thioester linkage.

For example, in the preparation of many acylated amino acids, the amino acids are dissolved in an aqueous alkaline solution of a metal hydroxide, e.g., sodium or potassium hydroxide and the acylating agent added. The reaction time can range from about 1 hour to about 4 hours, preferably about 2 to about 2.5 hours. The temperature of the mixture is maintained at a temperature generally ranging between about 5° C. and about 70° C., preferably between about 10° C. and about 50° C. The amount of alkali employed per equivalent of NH, groups in the amino acids generally ranges between about 1.25 moles and about 3 moles, and is preferably between about 1.5 moles and about 2.25 moles per equivalent of $NH_2$. The pH of the reaction solution generally ranges between about pH 8 and about pH 13, and is preferably between about pH 10 and about pH 12. The amount of amino modifying agent employed in relation to the quantity of amino acids is based on the moles of total free NH, in the amino acids. In general, the amino modifying agent is employed in an amount ranging between about 0.5 and about 2.5 mole equivalents, preferably between about 0.75 and about 1.25 equivalents, per molar equivalent of total NH, groups in the amino acids.

The modified amino acid formation reaction is typically quenched by adjusting the pH of the mixture with a suitable acid, e.g., concentrated hydrochloric acid, until the pH reaches between about 2 and about 3. The mixture separates on standing at room temperature to form a transparent upper layer and a white or off-white precipitate. The upper layer is discarded, and modified amino acids are collected by filtration or decantation. The crude modified amino acids are then mixed with water. Insoluble materials are removed by filtration, and the filtrate is dried in vacuo. The yield of modified amino acids generally ranges between about 30 and about 60%, and usually about 45%. The present invention also contemplates amino acids which have been modified by multiple acylation, e.g., diacylation, triacylation, etc.

If amino acid esters or amides are the starting materials, they are dissolved in a suitable organic solvent such as dimethylformamide or pyridine, and are reacted with the amino modifying agent at a temperature ranging between about 5° C. and about 70° C., preferably about 250° C., for a period ranging between about 7 and about 24 hours. The amount of amino modifying agents used relative to the amino acid esters are the same as described above for amino acids.

Thereafter, the reaction solvent is removed under negative pressure, and optionally, the ester or amide functionality can be removed by hydrolyzing the modified amino acid ester with a suitable alkaline solution, e.g., 1N sodium hydroxide, at a temperature ranging between about 50° C., and about 80° C., preferably about 70° C., for a period of time sufficient to hydrolyze off the ester group and form the modified amino acid having a free carboxyl group. The hydrolysis mixture is then cooled to room temperature and acidified, e.g., with an aqueous 25% hydrochloric acid solution, to a pH ranging between about 2 and about 2.5. The modified amino acid precipitates out of solution and is recovered by conventional means such as filtration or decantation.

The modified amino acids may be purified by acid precipitation, recrystallization, or fractionation on one or more solid chromatographic supports, alone or linked in tandem. Suitable recrystallization solvent systems include, but are not limited to, acetonitrile, methanol, and tetrahydrofuran. Fractionation may be performed on a suitable chromatographic support such as silica gel or alumina, using solvent mixtures such as methanol/n-propanol mixtures or acetic acid/butanol/water mixtures as the mobile phase; reverse phase column supports using trifluoroacetic acid/acetonitrile mixtures as the mobile phase, and ion exchange chromatography using water as the mobile phase. When anion exchange chromatography is performed, preferably a 0–500 mM sodium chloride gradient is employed. The modified amino acids may also be purified by extraction with a lower alcohol such as methanol, butanol, or isopropanol to remove impurities such as inorganic salts.

The modified amino acids generally are soluble in alkaline aqueous solution (pH≧9.0); partially soluble in ethanol, n-butanol and 1:1 (v/v) toluene/ethanol solution; and insoluble in neutral water. The alkali metal salts, e.g., the sodium salts of the modified amino acids, are generally soluble in water at about a pH of 6–8.

In poly amino acids or peptides, one or more of the amino acids may be modified acylated and/or sulfonated. Poly amino acids and peptides may include one or more acylated amino acid(s). Although linear modified poly amino acids and peptides will generally include only one acylated amino acid, other poly amino acid and peptide configurations can include more than one acylated amino acid. Poly amino acids and peptides can be polymerized with the acylated amino acid(s) or can be acylated after polymerization.

Delivery Systems

The compositions of the present invention may include one or more active agents.

In one embodiment, the compounds above or salts of these compounds or poly amino acids or peptides that include at least one of these compounds or salts may be used directly as a delivery carrier by simply mixing one or more compounds or salts, poly amino acids or peptides with the active agent prior to administration.

The administration mixtures are prepared by mixing an aqueous solution of the carrier with an aqueous solution of the active ingredient, just prior to administration. Alternatively, the carrier and the biologically or chemically active ingredient can be admixed during the manufacturing process. The solutions may optionally contain additives such as phosphate buffer salts, citric acid, acetic acid, gelatin, and gum acacia.

Stabilizing additives may be incorporated into the carrier solution. With some drugs, the presence of such additives promotes the stability and dispersibility of the agent in solution. The stabilizing additives may be employed at a concentration ranging between about 0.1 and 5% (w/v), preferably about 0.5% (w/v). Suitable, but non-limiting examples of stabilizing additives include gum acacia, gelatin, methyl cellulose, polyethylene glycol, carboxylic acids and salts thereof, and polylysine. The preferred stabilizing additives are gum acacia, gelatin, and methyl cellulose.

The amount of active agent is an amount effective to accomplish the purpose of the particular active agent for the target indication. The amount of active agent in the compositions typically is a pharmacologically, biologically, therapeutically, or chemically effective amount. However, the amount can be less than a pharmacologically, biologically, therapeutically, or chemically effective amount when the composition is used in a dosage unit form, such as a capsule, a tablet, a powder, or a liquid, because the dosage unit form may contain a plurality of carrier/biologically or chemically active agent compositions of may contain a divided pharmacologically, biologically, therapeutically, or chemically effective amount. The total effective amount can then be administered in cumulative units containing, in total, pharmacologically, biologically, therapeutically or chemically active amounts of biologically or pharmacologically active agent.

The total amount of active agent, and particularly biologically or chemically active agent, to be used can be determined by those skilled in the art. However, it has surprisingly been found that with some biologically or chemically active agents, the use of the presently disclosed carriers provides extremely efficient delivery, particularly in oral, intranasal, sublingual, intraduodenal, subcutaneous, buccal, intracolonic, rectal, vaginal, mucosal, pulmonary, transdermal, intradermal, parenteral, intravenous, intramuscular, and ocular systems, as well as traversing the blood-brain barrier. Therefore, lower amounts of biologically or chemically active agents than those used in prior dosage unit forms or delivery systems can be administered to the subject, while still achieving the same blood levels and therapeutic effects.

The amount of carrier in the present compositions is a delivery effective amount and can be determined for any particular carrier or biologically or chemically active agent by methods known to those skilled in the art. The effective amounts of the active agent and carrier in the composition may vary over a considerable range and is dependent upon the age, weight, sex, sensitivity, medical history, and the like of the individual. Clearly, it is necessary to take into account the nature of the active agent and carrier, the specific activity of the agent (units of bioactivity/mass), and its rate of absorption in the gastrointestinal tract, all of which contribute to a determination of the therapeutically effective dose.

Following administration, the active agent present in the composition or dosage unit form is rapidly taken up into the circulation. The bioavailability of the ingested agent is readily assessed by measuring a known pharmacological activity in blood, e.g. an increase in blood clotting time caused by heparin, or a decrease in circulating calcium levels caused by calcitonin.

Dosage unit forms can also include any of excipients, diluents, disintegrants, lubricants, plasticizers, colorants, flavorants, taste-masking agents, sugars, sweeteners, salts, and dosing vehicles, including, but not limited to water, 1,2-propane diol, ethanol, olive oil, or any combination thereof.

The delivery compositions of the present invention may also include one or more enzyme inhibitors. Such enzyme inhibitors include, but are not limited to, compounds such as actinonin or epiactinonin and derivatives thereof. Derivatives of these compounds are disclosed in U.S. Pat. No. 5,206,384, the disclosure of which is hereby incorporated herein by reference. Other enzyme inhibitors include, but are not limited to, aprotinin (Trasylol) and Bowman-Birk inhibitor.

The system is particularly advantageous for delivering chemically or biologically active agents which would otherwise be destroyed or rendered less effective by conditions encountered before the active agent reaches its target zone (i.e. the area in which the active agent of the delivery composition is to be released) and within the body of the animal to which they are administered. Particularly, the present invention is useful in pulmonary administration, such as by an inhaler, of active agents, especially those which are not ordinarily deliverable by that route or those for which improved delivery is desired. Improved delivery may be faster delivery or greater delivery in a given time period.

DESCRIPTION OF THE PREFERRED EMBODIMENTS

The following examples illustrate the invention without limitation. All parts are given by weight unless otherwise indicated.

EXAMPLE 1

Preparation of 2-(4-(N-salicyloyl)aminophenyl) propionic Acid

A slurry of 58.6 g (0.355 mol) of 2-(4-aminophenyl) propionicacid and 500 ml of methylene chloride was treated with 90.11 ml (77.13 g, 0–710 mol) of trimethylsilyl chloride and was heated to reflux for 120 min. The reaction mixture was cooled to 0° C. and treated with 184.44 ml (107.77 g, 1.065 mol) of triethylamine. After stirring for 5 minutes, this mixture was treated with a solution of 70.45 g (0.355 mol) of O-acetylsalicyloyl chloride and 150 ml of methylene chloride. The reaction mixture was warmed to 25° C. and stirred for 64 hr. The volatiles were removed in vacuo. The residue was stirred in 2N aqueous sodium hydroxide for one hour and acidified with 2 M aqueous sulfuric acid. The solid was recrystallized twice from ethanol/water to give a tan solid. Isolation by filtration afforded 53.05 g of (52% yield) of 2-(4-(N-salicyloyl)aminophenyl)propionic acid.

Properties

Solubility: 200 mg/ml: 200 mg+350 µl 2N NaOH+650 µl $H_2O$-pH-7.67. Anal. calculated for —C,67.36; H, 5.3; N, 4.91. Found —C, 67.05; H, 5.25; N, 4.72.

EXAMPLE 2

Preparation of Sodium 2-(4-(N-salicyloyl) aminophenyl)progionate

A solution of 53.05 g (0.186 mol) of 2-(4-(N-salicyloyl)aminophenyl)propionic acid and 300 ml of ethanol was treated with 7.59 g (0.190 mol) of NaOH dissolved in 22 ml of water. The reaction mixture was stirred for 30 min at 25C. and for 30 min at 0° C. The resulting pale yellow solid was isolated by filtration to give 52.61 g of sodium 2-(4-(N-salicyloyl)aminophenyl)propionate.

Properties

Solubility: 200 mg/ml clear solution, pH=6.85. Anal. calculated for —C, 60.45; H, 5.45; N, 3.92; Na, 6.43. Found —C, 60.84; H, 5.87; N, 3.85; Na, 6.43. Melting point 236–238° C.

EXAMPLE 3

A pulmonary delivery dosing composition of 0.1 mg/kg of porcine insulin and 7.5 mg/kg of the compound of Example 2 in water was prepared. A O.3 ml/kg dose of the pulmonary dosing composition at pH 7.3–7.6 was administered to five normal, non-fasting rats by the following procedure. 1½ Popper and Sons gavage needles were inserted about a few centimeters down the animals' throats. The tip of the needed was manipulated towards the animals' ventral sides where the needle could fall into a pocket and then with further manipulation the trachea. Once the needle was in the trachea, the dosing solution was delivered through the needle.

Periodic blood samples were drawn via the tail artery, and blood glucose levels were measured using Ektachem DT slides (Johnson & Johnson Clinical Diagnostics, Inc., Rochester N.Y.).

Figure 1:
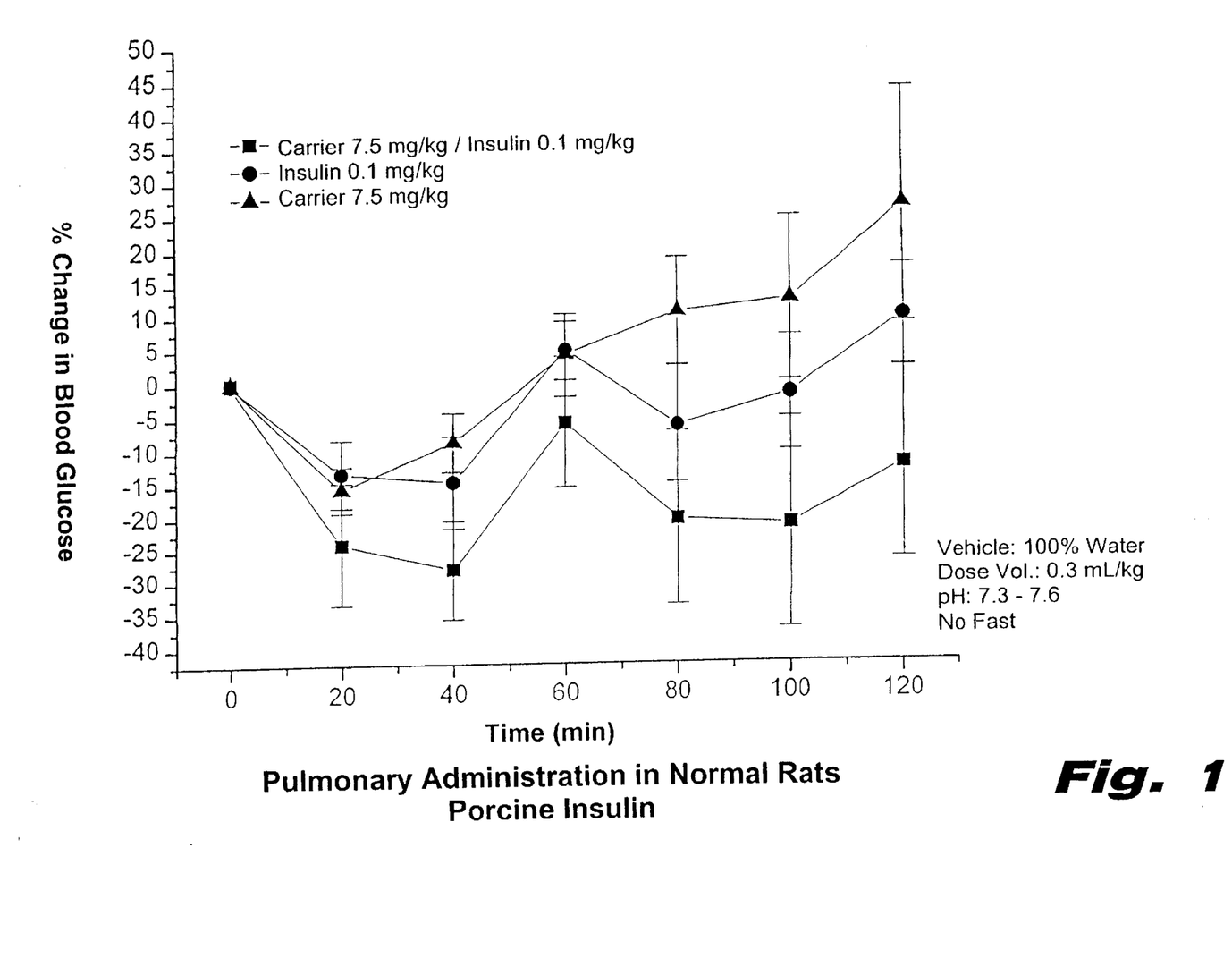
FIG. 1 is a graphical illustration of blood glucose levels after pulmonary delivery of insulin.

Results are illustrated in FIG. 1.

Comparative Example 3A

The procedure of Example 3 was followed, substituting a dosing composition of 0.1 mg/kg of porcine insulin and water for the dosing composition.

Results are illustrated in FIG. 1.

Comparative Example 3B

The procedure of Example 3 was followed, substituting a dosing solution of 7.5 mg/kg of the compound prepared in Example 1 in water for the dosing solution.

Results are illustrated in FIG. 1.

EXAMPLE 4

The procedure of Example 3 was followed, substituting a dosing composition of 0.5 mg/kg of porcine insulin and 7.5 mg/kg of the compound prepared in Example 2, in water for the dosing composition at pH 6.6–6.9.

Figure 2:
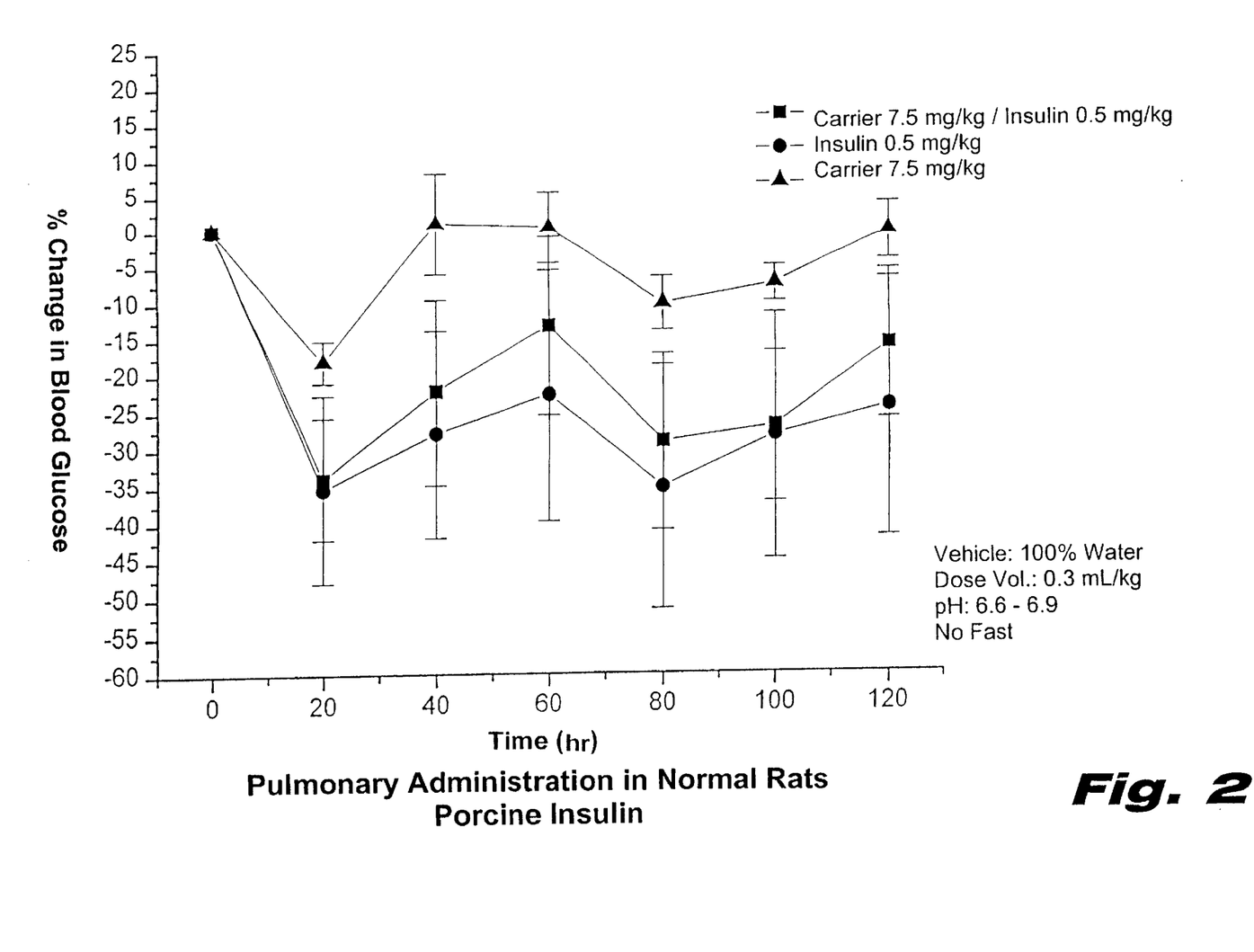
FIG. 2 is a graphical illustration of blood glucose levels after pulmonary delivery of insulin.

Results are illustrated in FIG. 2.

Comparative Example 4A

The procedure of Example 4 was followed, substituting a dosing composition of 0.5 mg/kg of porcine insulin in water for the dosing composition.

Results are illustrated in FIG. 2.

Comparative Example 4B

The procedure of Example 4 was followed, substituting a dosing composition of 7.5 mg/kg of the compound prepared in Example 2 in water for the dosing solution.

Results are illustrated in FIG. 2.

EXAMPLE 5

A dosing composition of 300 mg/kg of the compound prepared in Examples 2 and 3 mg/kg of human insulin in water at pH 7.02 was prepared. Strept catherized rats were dosed by oral gavage with 1 ml/kg of the dosing composition. Blood glucose levels (mg/dL) were measured.

Results are illustrated in Table 1 below.

TABLE 1

| Time (hrs): | 0 | 0.5 | 1 | 2 | 3 | 4 |
|---|---|---|---|---|---|---|
| Assay: | 0 | −44.9 | −42.59 | −37.58 | 36.62 | −29.88 |
| SD: | 0 | 13.88 | 28.33 | 30.87 | 26.27 | 18.61 |

EXAMPLE 6

A dosing composition of 300 mg/kg of the compound prepared in Example 1 and 100 Mg/kg of the N-terminal fragment of parathyroid hormone (amino acids 1–34) in water at pH 8.13 was prepared. Normal rats were dosed by oral gavage with 1 ml/kg of the dosing composition. Serum levels of parathyroid hormone (pg/mL) were measured.

Results are illustrated in in Table 2 below.

TABLE 2

| Time(mins): | 0 | 15 | 30 | 45 | 60 | 90 |
|---|---|---|---|---|---|---|
| Assay: | 0 | 1522.53 | 886.5 | 786.46 | 711.6 | 482.46 |
| SD: | 0 | 538.5 | 272.21 | 239.78 | 181.65 | 329.78 |

EXAMPLE 7

A dosing composition of 100 mg/kg of the compound prepared in Example 1 and 200 ug/kg of the N-terminal fragment of parathyroid hormone (amino acids 1–34) in water at pH 7.65 was prepared. Normal rats were dosed by oral gavage with 1 mg/kg of the dosing composition. Serum levels of parathyroid hormone (pg/mL) were measured.

Results are illustrated in Table 3 below.

TABLE 3

| Time(mins): | 0 | 15 | 30 | 45 | 60 | 90 |
|---|---|---|---|---|---|---|
| Assay: | 0 | 929.6 | 767.27 | 986.79 | 411.03 | 356.8 |
| SD: | 0 | 693.18 | 525.18 | 1211.9 | 136.15 | 61.13 |

EXAMPLE 8

The method of Example 7 was followed but the pH of the dosing composition was 7.55.

Results are illustrated in Table 4 below.

TABLE 4

| Time(mins): | 0 | 15 | 30 | 45 | 60 | 90 |
|---|---|---|---|---|---|---|
| Assay: | 0 | 976.79 | 711.42 | 610.78 | 520.51 | 516.19 |
| SD: | 0 | 388.07 | 244.89 | 218.16 | 78.31 | 37.6 |

EXAMPLE 9

Pulmonary Insulin Delivery

The carrier compound 2-(4-(N-salicyloyl)aminophenyl) propionic acid was tested as follows. Each rat was weighed and identified using an indelible marker and anesthetized by intramuscular injection of thorazine (3 mg/kg) and ketamine (44 mg/kg).

An endotracheal tube (spray instillator from Penn Century of Philadelphia, Pa.) with a syringe (Hamilton syringe) attached to the endotracheal tube was inserted using a fiber optic laryngoscope. The syringe (Hamilton syringe) of the instillator was used to instill insulin (0.03 mg/kg) and a carrier compound (16 mg/kg) into the lower portions of the airway. The endotracheal tube was removed following administration, and the breathing rate was monitored throughout the remainder of the study.

Blood samples were withdrawn at 0, 5, 15, 30, 60, and 120 minutes via the tail artery and assayed with a DSL Insulin Kit #10-1600 following the procedure outlined in the kit. The $C_{max}$ value with the carrier was 44.6±10.0. The $C_{max}$ value without the carrier was 19.4±4.3.

EXAMPLE 10

Recombinant Human Growth Hormone (rhGH) Oral Delivery

Oral gavage (PO) dosing solutions containing 200 mg/kg carrier compound 2-(4-(N-salicyloyl)aminophenyl) propionic acid and 3 mg/kg rhGH in 100% phosphate buffer were prepared by mixing. The pH of the solutions ranged from about 7.67 to about 8.09.

Male Sprague-Dawley rats weighing 200–250 g were fasted for 24 hours and administered ketamine (44 mg/kg) and chlorpromazine (1.5 mg/kg) 15 minutes prior to dosing. The rats were administered 1 ml/kg of the dosing solution by PO. Blood samples were collected parenterally from the tail artery for determination of serum rHGH concentrations. Serum rHGH concentrations were quantified by an rHGH immunoassay test kit (Kit #K1F4015 from Genzyme Corporation Inc., Cambridge, Mass.). The mean peak serum concentration of rHGH was 93±74 ng/ml.

EXAMPLE 11

Erythropoietin (EPO) Oral Delivery

Oral gavage (PO) dosing solutions containing 200 mg/kg carrier compound 2-(4-(N-salicyloyl)aminophenyl) propionic acid and 1 mg/kg human erythropoietin quantikine IUD in 100% water were prepared by mixing. The pH of the solutions ranged from about 6.9 to about 7.9.

Male Sprague-Dawley rats weighing 200–250 g were fasted for 24 hours and administered ketamine (44 mg/kg) and chlorpromazine (1.5 mg/kg) 15 minutes prior to dosing. The rats were administered 1 ml/kg of the dosing solution by PO. Blood samples were collected parenterally from the tail artery for determination of serum EPO concentrations. Serum EPO concentrations were quantified by an Elisa assay test kit (Kit #DEPOO from R&D Systems, Minneapolis, Minn.). The mean peak serum concentration of EPO was 163±136 ng/ml.

The procedure was repeated without the carrier compound. The mean peak serum concentration of EPO was 0 ng/ml.

The above mentioned patents, applications, test methods, and publications are hereby incorporated by reference in their entirety.

Many variations of the present invention will suggest themselves to those skilled in the art in light of the above detailed description. All such obvious variations are within the full intended scope of the appended claim.

What is claimed is:

1. A salt of the compound having the formula wherein the salt is not a sodium salt.

2. A composition comprising:
   (A) at least one active agent; and
   (B) a carrier comprising a compound having the formula or salt thereof.

3. A composition as defined in claim 2, wherein said active agent is selected from the group consisting of a biologically active agent, a chemically active agent, or a combination thereof.

4. A composition as defined in claim 3, wherein said biologically active agent comprises at least one peptide, mucopolysaccharide, carbohydrate, or lipid.

5. A composition as defined in claim 3, wherein said biologically active agent is selected from the group consisting of growth hormones, human growth hormones (hGH), recombinant human growth hormones (rhGH), bovine growth hormone, porcine growth hormones, growth hormone-releasing hormones, interferons, α-interferon, β-interferon, γ-interferon, interleukin-1, interleukin-II; insulin, insulin-like growth factor(IGF), IGF-1, heparin, unfractionated heparin, heparinoids, dermatans, chondroitins, low molecular weight heparin, very low molecular weight heparin, ultra low molecular weight heparin, calcitonin, salmon calcitonin, eel calcitonin, human calcitonin, erythropoietin (EPO), atrial naturetic factor, antigens, monoclonal antibodies, somatostatin, protease inhibitors, adrenocorticotropin, gonadotropin releasing hormone, oxytocin, leutinizing-hormone-releasing-hormone, follicle stimulating hormone, glucocerebrosidase, thrombopoietin, filgrastim, prostaglandins, cyclosporin, vasopressin, sodium chromoglycate, disodium chromoglycate, vancomycin, desferrioxamine (DFO), parathyroid hormone (PTH), fragments of PTH, antimicrobials, anti-fungal agents, analogs, fragments, mimetics and polyethylene glycol (PEG)-modified derivatives of these compounds; and any combination thereof.

6. A composition as defined in claim 3, wherein said biologically active agent is selected from the group consisting of human growth hormones (hGH), bovine growth hormone, growth hormone-releasing hormones, interferons, interleukin-1, interleukin-II, insulin, heparin, low molecular weight heparin, very low molecular weight heparin, calcitonin, erythropoietin (EPO), atrial naturetic factor, antigens, monoclonal antibodies, somatostatin, adrenocorticotropin, gonadotropin releasing hormone, oxytocin, vasopressin, sodium chromoglycate, disodium chromoglycate, vancomycin, desferrioxamine (DFO), parathyroid hormone (PTH), antimicrobials, anti-fungal agents, and any combination thereof.

7. A composition as defined in claim 3, wherein said biologically active agent comprises an interferon, interleukin-II, insulin, heparin, low molecular weight heparin, very low molecular weight heparin, calcitonin, parathyroid hormone (PTH), erythropoietin (EPO), human growth hormone (hGH), oxytocin, vasopressin, vancomycin, desferrioxamine (DFO), parathyroid hormone, and combinations thereof.

8. A composition as defined in claim 3, wherein said biologically active agent comprises unfractionated heparin, ultra low molecular weight heparin, and combinations thereof.

9. A composition as defined in claim 3, wherein said biologically active agent comprises insulin.

10. A composition as defined in claim 3, wherein said biologically active agent comprises parathyroid hormone.

11. A composition as defined in claim 3, wherein said biologically active agent comprises human growth hormone.

12. A composition as defined in claim 3, wherein said biologically active agent comprises erythropoietin.

13. A composition as defined in claim 2, wherein said carrier comprises a poly(amino acid) or a polypeptide.

14. A dosage unit form comprising:
(A) a composition as defined in claim 2; and
(B)
  (a) an excipient
  (b) a diluent,
  (c) a disintegrant,
  (d) a lubricant,
  (e) a plasticizer,
  (f) a colorant,
  (g) a dosing vehicle, or
  (h) any combination thereof.

15. A dosage unit form as defined in claim 13, wherein said active agent is selected from the group consisting of a biologically active agent, a chemically active agent, or a combination thereof.

16. A dosage unit form as defined in claim 14, wherein said biologically active agent comprises at least one peptide, mucopolysaccharide, carbohydrate, or lipid.

17. A dosage unit form as defined in claim 14, wherein said biologically active agent is selected from the group consisting of growth hormones, human growth hormones (hGH), recombinant human growth hormones (rhGH), bovine growth hormone, porcine growth hormones, growth hormone-releasing hormones, interferons, α-interferon, β-interferon, γ-interferon, interleukin-1, interleukin-II, insulin, insulin-like growth factor(IGF), IGF-1, heparin, unfractionated heparin, heparinoids, dermatans, chondroitins, low molecular weight heparin, very low molecular weight heparin, ultra low molecular weight heparin, calcitonin, salmon calcitonin, eel calcitonin, human calcitonin, erythropoietin (EPO), atrial naturetic factor, antigens, monoclonal antibodies, somatostatin, protease inhibitors, adrenocorticotropin, gonadotropin releasing hormone, oxytocin, leutinizing-hormone-releasing-hormone, follicle stimulating hormone, glucocerebrosidase, thrombopoietin, filgrastim, prostaglandins, cyclosporin, vasopressin, sodium chromoglycate, disodium chromoglycate, vancomycin, desferrioxamine (DFO), parathyroid hormone (PTH), fragments of PTH, antimicrobials, anti-fungal agents, analogs, fragments, mimetics and polyethylene glycol (PEG)-modified derivatives of these compounds, and any combination thereof.

18. A dosage unit form as defined in claim 14, wherein said biologically active agent is selected from the group consisting of human growth hormones (hGH), bovine growth hormone, growth hormone-releasing hormones, interferons, interleukin-1, interleukin-II, insulin, heparin, low molecular weight heparin, very low molecular weight heparin, calcitonin, erythropoietin (EPO), atrial naturetic factor, antigens, monoclonal antibodies, somatostatin, adrenocorticotropin, gonadotropin releasing hormone, oxytocin, vasopressin, sodium chromoglycate, disodium chromoglycate, vancomycin, desferrioxamine (DFO), parathyroid hormone (PTH), antimicrobials, anti-fungal agents, and any combination thereof.

19. A dosage unit form as defined in claim 14, wherein said biologically active agent comprises an interferon, interleukin-II, insulin, heparin, low molecular weight heparin, very low molecular weight heparin, calcitonin, parathyroid hormone (PTH), erythropoietin (EPO), human growth hormone (hGH), oxytocin, vasopressin, vancomycin, desferrioxamine (DFO), parathyroid hormone, and combinations thereof.

20. A dosage unit form as defined in claim 14, wherein said biologically active agent comprises unfractionated heparin, ultra low molecular weight heparin, and combinations thereof.

21. A dosage unit form as defined in claim 14, wherein said biologically active agent comprises insulin.

22. A dosage unit form as defined in claim 14, wherein said biologically active agent comprises parathyroid hormone.

23. A dosage unit form as defined in claim 14, wherein said biologically active agent comprises human growth hormone.

24. A dosage unit form as defined in claim 14, wherein said biologically active agent comprises erythropoietin.

25. A dosage unit form as defined in claim 13, comprising a tablet, a powder, a capsule, or a liquid.

26. A method for administering a biologically-active agent to an animal in need of said agent, said method comprising administering orally to said animal a composition as defined in claim 3.

27. A method for preparing a composition comprising mixing:
(A) at least one active agent;
(B) the compound of claim 1; and
(C) optionally, a dosing vehicle.

* * * * *